United States Patent [19]
Brandon et al.

[11] Patent Number: 5,916,203
[45] Date of Patent: Jun. 29, 1999

[54] COMPOSITE MATERIAL WITH ELASTICIZED PORTIONS AND A METHOD OF MAKING THE SAME

[75] Inventors: Robert Griffiths Brandon; Franklin Mean-Chi Chen, both of Appleton; Robert Eugene Vogt, Neenah, all of Wis.

[73] Assignee: Kimberly-Clark Worldwide, Inc., Neenah, Wis.

[21] Appl. No.: 08/963,155

[22] Filed: Nov. 3, 1997

[51] Int. Cl.$^6$ .............................. A61F 13/15; H05B 6/64; B32B 5/16
[52] U.S. Cl. .................. 604/367; 604/373; 604/385.2; 219/730; 219/759; 442/110; 442/117; 428/323
[58] Field of Search ................................ 604/362, 373, 604/385.2; 219/730, 759; 428/323–331, 339; 442/110, 117, 131

[56] References Cited

U.S. PATENT DOCUMENTS

| | | | |
|---|---|---|---|
| 4,798,603 | 1/1989 | Meyer et al. | 604/378 |
| 4,808,252 | 2/1989 | Lash | 604/385.2 |
| 4,816,094 | 3/1989 | Pomplun et al. | 156/85 |
| 4,938,821 | 7/1990 | Soderlund et al. | 156/85 |
| 4,985,300 | 1/1991 | Huang | 428/332 |
| 5,176,668 | 1/1993 | Bernardin | 604/368 |
| 5,176,672 | 1/1993 | Bruemmer et al. | 604/385.1 |
| 5,192,606 | 3/1993 | Proxmire et al. | 428/284 |
| 5,220,141 | 6/1993 | Quick et al. | 219/10.55 E |
| 5,343,024 | 8/1994 | Prosise et al. | 219/730 |
| 5,362,504 | 11/1994 | Kamper et al. | 426/89 |
| 5,509,915 | 4/1996 | Hanson et al. | 604/378 |
| 5,536,921 | 7/1996 | Hedrick et al. | 219/693 |

*Primary Examiner*—Robert A. Clarke
*Attorney, Agent, or Firm*—Jeffrey B. Curtin

[57] ABSTRACT

A method of making a composite material having elasticized portions includes supplying a web of temperature sensitive elastic material, applying a microwave sensitive material to selected regions of the elastic material and subsecting the composite material to microwave energy. The microwave energy may be converted into heat by the microwave sensitive material thereby heating the microwave sensitive material and activating regions of the temperature sensitive elastic material adjacent the microwave sensitive material. The activated regions of the elastic material provide the elasticized portions in the composite material. Alternatively, the microwave sensitive material may reflect the microwave energy which may then directly heat and activate the regions of the elastic material opposite the selected regions to which the microwave sensitive material is applied. The method is particularly useful in the manufacture of garment-type articles such as disposable absorbent articles.

39 Claims, 3 Drawing Sheets

COMPOSITE MATERIAL WITH ELASTICIZED PORTIONS AND A METHOD OF MAKING THE SAME

BACKGROUND OF THE INVENTION

1. Field of the Invention

The present invention relates to materials having elasticized portions and methods of making the same. More particularly, the present invention relates to absorbent garments, such as disposable diapers and adult incontinence garments, which include such materials and which are configured to absorb and contain body exudates and prevent leakage.

2. Description of the Related Art

Elastic shirring of garments in selected regions is desirable or essential to conform the garment to the wearer's body such as at the waist or wrist. For example, conventional absorbent articles, such as disposable diapers, employ elasticized waistbands and leg cuffs to help conform the article to the wearer and reduce the leakage of body exudates. Some conventional absorbent articles have also included elasticized containment or barrier flaps at the leg or waist sections of the article to further reduce leaks.

To provide such elasticized portions, conventional garments have typically included individual strips or strands of elastic material which have been secured to the garment. Generally, the elastic material is applied to the garment in a stretched condition such that, when it is allowed to relax, the elastic material contracts and gathers predetermined portions of the garment. Conventional garments have otherwise included individual strips of latent elastic material along the leg or waist regions which are activated through the application of heat after they have been applied to the garment. In the garments described above, the individual elastic elements are generally applied using conventional cut and place technology which requires complex equipment to ensure the accurate placement of each element with respect to the other components of the garment.

However, many conventional garments which incorporate such elastic materials and the methods of making such garments have not been completely satisfactory. For example, it has been difficult to maintain the elastic materials in a stretched condition while consistently and accurately attaching such stretched elastic materials to the garment. This problem is particularly evident when attempting to attach the elastic materials in nonlinear configurations. Moreover, after such prestretched elastic materials are attached to a web of material, they tend to retract and bunch which has made it difficult to maintain accurate registration and control of the web of material throughout any additional processes such as the application of additional components to the garment.

Further, when individual heat activated elastic materials are used, the heat activation is generally accomplished by passing the garments through a heated air duct for a period of time. In such a configuration, it has typically taken several seconds to elevate the temperature of the elastic material sufficient to activate it and cause it to retract and gather the garment. As a result, such heating processes can consume vast amounts of energy and undesirably result in slower manufacturing speeds. Accordingly, there remains a need for improved garments having elasticized portions and, in particular, elasticized portions which are configured in a nonlinear manner and methods of making the same.

SUMMARY OF THE INVENTION

In response to the difficulties and problems discussed above, a new composite material having elasticized portions, a new absorbent article incorporating such composite material and a new method of making such composite material have been discovered.

In one aspect, the present invention relates to a composite material having elasticized portions. The composite material includes a temperature sensitive elastic material and a microwave sensitive material located on selected regions of the temperature sensitive elastic material. The elasticized portions in the composite material are provided by applying microwave energy to the composite material thereby activating the temperature sensitive elastic material adjacent the microwave sensitive material. In a particular embodiment, a ratio of a relative dielectric loss factor of the microwave sensitive material to a relative dielectric loss factor of the temperature sensitive elastic material is at least about 5.

In another aspect, the present invention concerns an absorbent article having elasticized portions. The absorbent article includes at least one temperature sensitive elastic material, an absorbent layer located in superposed relation to the temperature sensitive elastic material, and a microwave sensitive material located on selected regions of the temperature sensitive elastic material. The selected regions of the temperature sensitive elastic material are activated by applying microwave energy to the article thereby heating the microwave sensitive material to create the elasticized portions. In a particular embodiment, the elasticized portions of the absorbent article are located adjacent leg openings in the absorbent article.

In another aspect, the present invention relates to a method of making a composite material having elasticized portions. The method includes supplying a web of temperature sensitive elastic material, applying a microwave sensitive material to selected regions of the web of temperature sensitive elastic material to provide the composite material, and applying microwave energy to the composite material thereby activating the temperature sensitive elastic material adjacent the microwave sensitive material to create the elasticized portions in the composite material. The web of temperature sensitive elastic material may be continuously supplied at a speed of at least about 200 meters per minute.

In yet another aspect, the present invention concerns a method of making an absorbent article having elasticized portions comprising the steps of: a) continuously supplying at least one web of temperature sensitive elastic material; b) securing an absorbent layer in superposed relation to the web of temperature sensitive elastic material; c) applying a microwave sensitive material to selected regions of the web of temperature sensitive elastic material; d) applying microwave energy to the web of temperature sensitive elastic material; and e) intermittently severing the continuous web of temperature sensitive elastic material to provide the absorbent article. The microwave sensitive material is heated by the microwave energy thereby activating the selected regions of the web of temperature sensitive elastic material to create the elasticized portions in the absorbent article.

The various aspects of the present invention can advantageously provide an improved composite material and absorbent article having elasticized portions and methods of making the same. In particular, the present invention can provide a composite material which is manufactured using microwave energy to activate selected portions of a web of material and render such portions elastically retractable while not activating other portions of the web of material. The use of such microwave activation can result in a more energy efficient, cost effective process for producing such composite materials. The microwave energy is material specific and does not heat the other components. Thus, the energy is fully utilized in activating the selected portions of the temperature sensitive elastic material. Moreover, the equipment necessary to carry out such processes and make such materials can be much less complicated because it is easier to maintain registration and control of the materials as they pass through various manufacturing steps because the materials are not elastically activated until at least most of the steps have been completed. When the microwave sensitive material is in the form of a solution, it is easy to provide the desired curvilinear shapes to the elasticized portions using printing or spraying techniques which are more easily adaptable to such configurations when compared to conventional cut and place technology.

BRIEF DESCRIPTION OF THE DRAWINGS

The invention will be more fully understood and further advantages will become apparent when reference is made to the following detailed description of the invention and the accompanying drawings, in which.

DETAILED DESCRIPTION OF THE INVENTION

The following detailed description of a composite material and article and methods of making the same of the present invention will be made in the context of a disposable diaper article which is adapted to be worn by infants about the lower torso. It is readily apparent, however, that the methods and materials of the present invention would also be suitable for use in the manufacture of other types of garments, such as general clothing garments, hospital gowns, and the like as well as other absorbent articles such as feminine care pads, incontinence garments, training pants, and the like. In addition, the invention will be described in the context of its various configurations. It should be appreciated that alternative arrangements of the invention can comprise any combination of such configurations.

Figure 1:
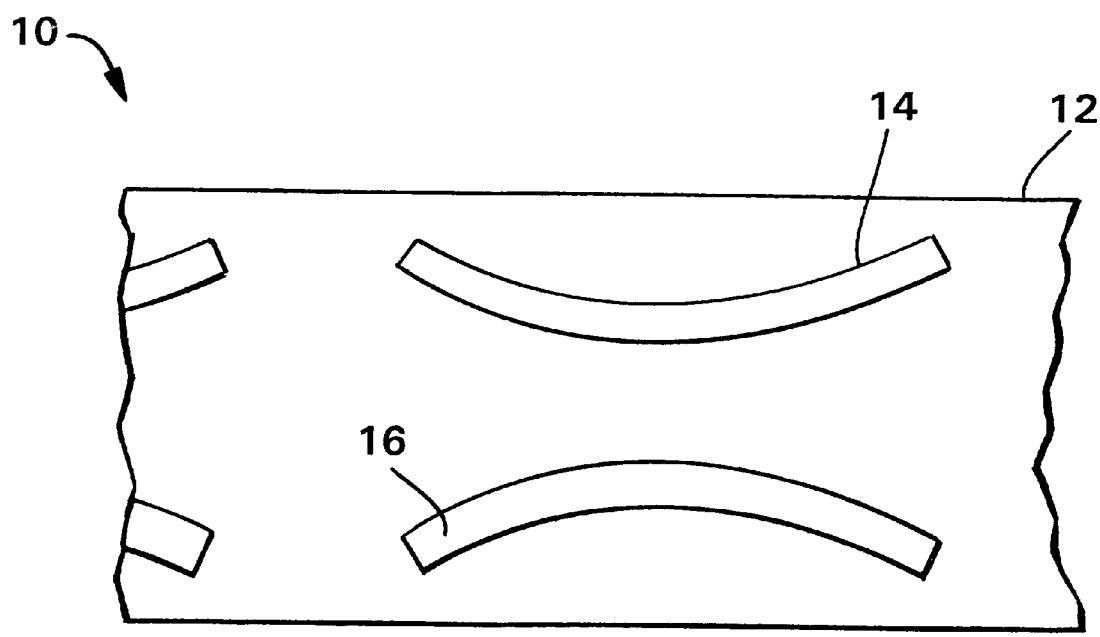
FIG. 1 representatively shows a top plan view of a composite material according to one embodiment of the invention.

A composite material having elasticized portions according to the present invention which may be suitable for use in a garment article is representatively illustrated in FIG. 1. The composite material 10 includes a temperature sensitive elastic material 12 which is generally in a latent, nonactivated state at ambient conditions. The composite material 10 further includes a microwave sensitive material 14 located on selected regions of the elastic material 12. The elasticized portions 16 of the composite material 10 are provided by applying microwave energy to the composite material 10. The microwave energy may be either absorbed or reflected by the microwave sensitive material 14.

If the microwave sensitive material 14 absorbs and converts the incident microwave energy into heat, the temperature of the microwave sensitive material 14 will increase to a point which causes the selected regions of the temperature sensitive elastic material 12 in contact with the heated material 14 to reach their relaxation temperature and retract or elastically activate. In general, when the selected regions of the temperature sensitive elastic material 12 reach the relaxation temperature of the material, they retract and become elastically activated. The amount of retraction is dependent upon the type of material and its sensitivity to microwave energy, the temperature to which the material is heated and the manner in which it is allowed to relax while being cooled.

Alternatively, if the microwave sensitive material 14 reflects the microwave energy, the regions of the temperature sensitive elastic material 12 opposite the selected regions to which the microwave sensitive material 14 is applied, will absorb and convert the incident microwave energy into heat. As a result, such opposite regions will increase in temperature to a point which causes the elastic material 12 in such regions to reach its relaxation temperature and retract or elastically activate. Thus, the different affect of the incident microwave energy on the elastic material 12 and the microwave sensitive material 14 allows the retraction and elastic activation of predetermined selected regions of the elastic material 12. In the absence of the microwave sensitive material 14, the entire elastic material 12 would either be activated or not when subjected to microwave energy depending upon the amount of energy used.

The temperature sensitive elastic material 12, as representatively illustrated in FIG. 1, can be any elastic material which is latent until it is heated to its relaxation temperature. A suitable elastic material may be manufactured from a wide selection of web materials, such as film materials, nonwoven materials, foam materials, natural fibers, synthetic fibers (for example, polyester or polypropylene fibers), or a combination of natural and synthetic fibers, or multiple threads of such materials. Various woven and nonwoven fabrics can be used for the elastic material 12. For example, the temperature sensitive elastic material 12 may be composed of a film or nonwoven web of polyolefin fibers such as, for example, a latent metallocene polymeric film.

The temperature sensitive elastic material 12 may define any relaxation temperature which allows selected activation of the material. For example, suitable materials may define a relaxation temperature of from about 50 to about 110 degrees Centigrade and desirably from about 70 to about 90 degrees Centigrade. The material employed to provide the elastic material 12 generally will exhibit a heat shrinkage of at least about 15 percent desirably at least about 50 percent and more desirably from about 100 to about 200 percent when subjected to a sufficient amount of microwave energy.

In a particular embodiment of the present invention, the elastic material 12 comprises an elastomeric material commercially available from Elf Atochem a business having offices in Philadelphia, Pa., under the trade designation PEBAX. In general, such a material comprises a segmented block copolymer having alternate segments of polyamide and polyether block polymers. For example, such material may include a poly(ethylene-oxide)-co-poly(amide) copolymer and a poly(ethylene-hexene) copolymer. Such a material may have a basis weight of about 50 grams per square meter and a density of about 1.01 grams per cubic centimeter. Alternatively, the elastic material 12 may comprise a latent metallocene catalyzed polyolefin elastomer commercially available from Exxon Corporation, a business having offices located in Houston, Texas, under the trade designation EXACT 4003. Such a polyolefin elastomer film defines a basis weight of about 50 grams per square meter and a density of about 0.865 grams per cubic centimeter.

Suitable materials for the temperature sensitive elastic material 12 can be provided by means well known to those skilled in the art. In general, the material 12 may be provided by subjecting the material to uniaxial tensioning to stretch the material to an elongated length significantly greater than that length at which permanent deformation occurs. Upon removal of the tension, the material will relax to a length greater than the original length corresponding to the amount of permanent deformation. Thus, the difference between the original prestretched length and the permanent deformation length is then available for retraction upon the application of the microwave energy.

The microwave sensitive material 14, as representatively illustrated in FIG. 1, can be any material which is affected by microwave energy. For example, the microwave sensitive material 14 may act as a susceptor and absorb the microwave energy thereby increasing in temperature. Alternatively, the microwave sensitive material 14 may reflect the microwave energy such that it and the areas of the elastic material 12 adjacent thereto do not appreciably change in temperature. When the composite material 10 of the present invention may be used in garment type articles, it is desirable that the microwave sensitive material 14 not degrade the appearance or feel of the elastic material 12.

A suitable microwave sensitive material 14 may be in a variety of forms. For example, the microwave sensitive material 14 may be a coating or layer of an adhesive or a liquid solution comprising ingredients which convert at least a portion of the incident microwave energy into heat. Suitable ingredients include polyacrylate solutions, polyacrylic acid solutions, polyvinyl methyl ether solutions, polyamide solutions and polyamide or polyvinyl methyl based hot melt adhesives. Other suitable ingredients include conductive ink solutions such as, for example, carbon based inks and metal based inks such as nickel or silver based inks. The application of such a liquid solution, ink solution or adhesive can be accomplished by many means known to those skilled in the art which are typically readily configured to apply the solution in any shape to provide the selected regions which are intended to be elasticized. Such known application processes generally have limited adverse impact on the materials being processed. Alternatively, the material 14 may be manufactured from a wide selection of web materials, such as film materials, nonwoven materials, foam materials, natural fibers, synthetic fibers, or combinations thereof which are sensitive to microwave energy.

The temperature sensitive elastic material 12 and the microwave sensitive material 14 of the different aspects of the present invention define relative dielectric loss factors different from each other such that they are affected differently when subjected to microwave energy. In general, the relative dielectric loss factor of a material indicates the ability of the material to generate heat via friction between the polar moieties of the material and the medium and between the ionic conducting species and the medium in the oscillating electromagnetic field.

For example, the microwave sensitive material 14 may define a relative dielectric loss factor which is greater than the relative dielectric loss factor of the temperature sensitive material 12. In such a configuration, the temperature of the microwave sensitive material 14 will increase more rapidly than the temperature of the elastic material 12 when subjected to microwave energy because the microwave sensitive material will convert more of the incident microwave energy into heat. As the temperature of the microwave sensitive material 14 increases so does the temperature of the elastic material which is adjacent to or in contact with the microwave sensitive material 14. Thus, the amount of microwave energy can be controlled such that only the selected regions of the elastic material 12 adjacent or in contact with the microwave sensitive material 14 reach the relaxation temperature of the elastic material and become elastically activated.

Alternatively, the microwave sensitive material 14 may define a relative dielectric loss factor which is less than the relative dielectric loss factor of the temperature sensitive material 12. In such a configuration, the temperature of the elastic material 12 will increase more rapidly than the temperature of the microwave sensitive material 14 when subjected to microwave energy because the elastic material will more readily convert the incident microwave energy into heat. As a result, the temperature of the elastic material 12 in contact with the microwave sensitive material 14 will not rise as rapidly as the remaining regions of the elastic material 12 not in contact with the microwave sensitive material 14. Thus, the microwave energy can be controlled to selectively activate only those regions of the elastic material 12 not in contact with the microwave sensitive material 14.

For use in the garment type articles of the present invention, it is generally desirable that the microwave sensitive material 14 function as a susceptor to attract and convert the incident microwave energy into heat for improved control. In such a configuration, the temperature sensitive elastic material 12 may generally define a relative dielectric loss factor of from about 0.0001 to about 0.1 and desirably from about 0.001 to about 0.1 and the microwave sensitive material 14 may generally define a relative dielectric loss factor of from about 0.1 to about 1000 and desirably from about 0.1 to about 100. However, the difference between the relative dielectric loss factors of the elastic material 12 and the microwave sensitive material 14 must be sufficient such that the selected elasticized portions 16 can be provided. In a particular embodiment, it is desired that the ratio of the relative dielectric loss factors of the microwave sensitive material 14 to the elastic material 12 be at least about 5 and desirably at least about 10 for improved process control.

The microwave sensitive material 14 may be applied by any conventional means, such as spraying, printing, brush coating or the like if the material is a liquid or by conventional application means known to those skilled in the art if the material 14 is a web material. The microwave sensitive material 14 may also be selectively or intermittently applied to particular sections of the elastic material 12, such as the side edges, to provide elasticity to such sections. The amount of microwave sensitive material 14 applied to the elastic material 12 will depend upon the materials and amount of microwave energy being used and the speed of the web of elastic material 12.

After subjecting the composite material 10 to microwave energy, the composite material defines selected portions which have retracted and activated to render them elastically contractible. Such elasticized portions may define an elongation of at least about 25 percent, desirably at least about 50 percent and more desirably from about 50 to about 150 percent. Typically, the nonactivated portions of the elastic material 12 are not elastically extensible to a great extent and generally define an elongation of less than about 20 percent. In a particular embodiment, a ratio of the elongation of the elasticized portions to the nonactivated portions is at least about 5 and desirably at least about 10.

Figure 2:
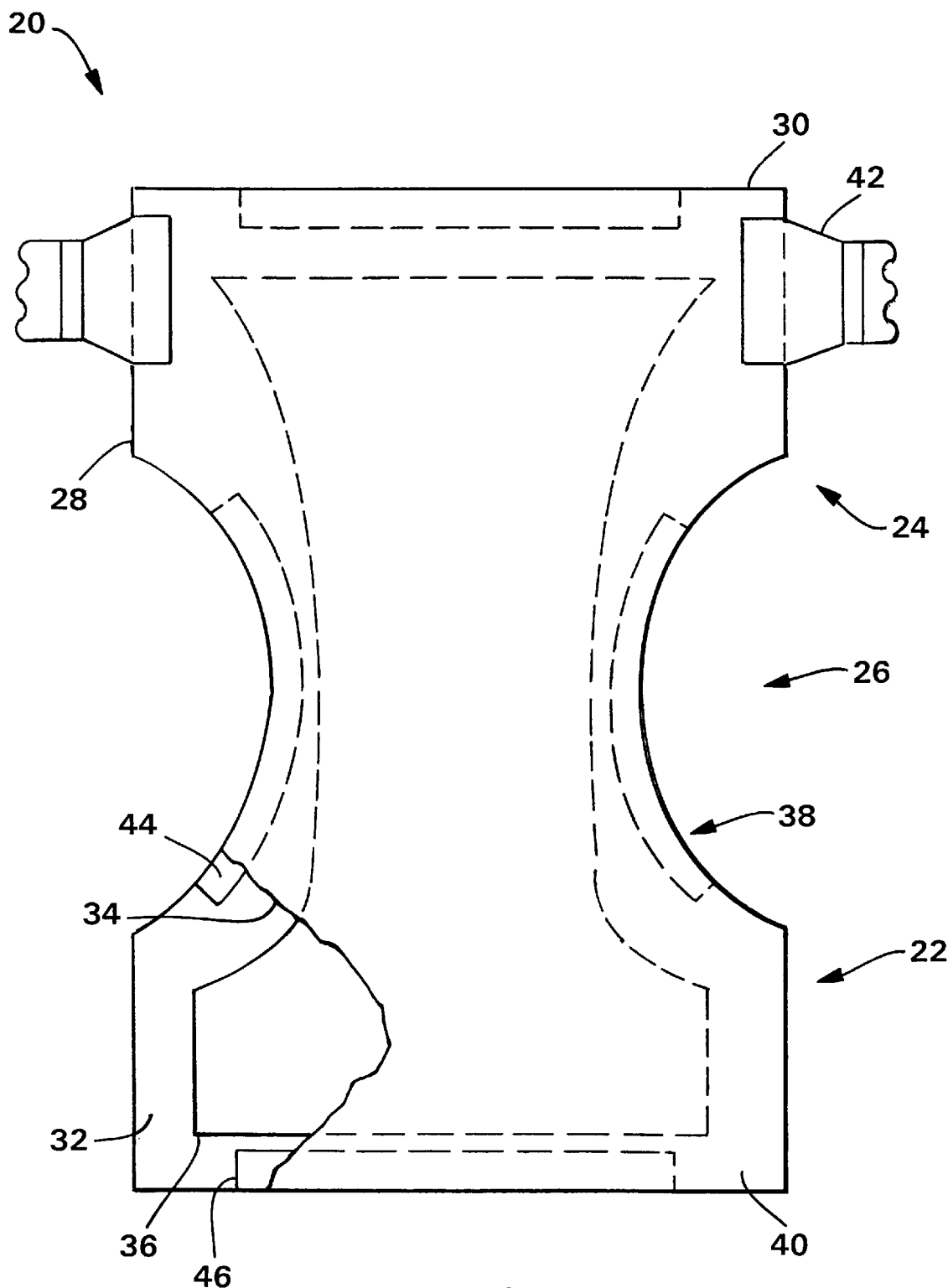
FIG. 2 representatively shows a partially cut away, top plan view of an absorbent article according to one embodiment of the invention.

With reference to FIG. 2, an integral absorbent garment article, such as the disposable diaper 20, includes the composite material 10 of the present invention and generally defines a front waist section 22, a rear waist section 24, an intermediate section 26 which interconnects the front and rear waist sections, a pair of laterally opposed side edges 28, and a pair of longitudinally opposed end edges 30. The front and rear waist sections include the general portions of the article which are constructed to extend substantially over the wearers front and rear abdominal regions, respectively, during use. The intermediate section of the article includes the general portion of the article which is constructed to extend through the wearer's crotch region between the legs. The opposed side edges 28 define leg openings for the diaper and generally are curvilinear or contoured to more closely fit the legs of the wearer. The opposed end edges 30 define a waist opening for the diaper 20 and typically are straight but may also be curvilinear.

FIG. 2 is a representative plan view of the diaper 20 of the present invention in a flat, uncontracted state. Portions of the structure are partially cut away to more clearly show the interior construction of the diaper 20, and the surface of the diaper which contacts the wearer is facing the viewer. The diaper 20 includes a substantially liquid impermeable outer cover 32, a porous, liquid permeable bodyside liner 34 positioned in facing relation with the outer cover 32, and an absorbent body 36, such as an absorbent pad, which is located between the outer cover and the bodyside liner. Marginal portions of the diaper 20, such as marginal sections of the outer cover 32, may extend past the terminal edges of the absorbent body 36. In the illustrated embodiment, for example, the outer cover 32 extends outwardly beyond the terminal marginal edges of the absorbent body 36 to form side margins 38 and end margins 40 of the diaper 20. The bodyside liner 34 is generally coextensive with the outer cover 32 but may optionally cover an area which is larger or smaller than the area of the outer cover 32, as desired.

The diaper 20, as representatively illustrated in FIG. 2, may further include a pair of fasteners 42 which are employed to secure the diaper 20 about the waist of a wearer. Suitable fasteners 42 include hook-and-loop type fasteners, adhesive tape fasteners, buttons, pins, snaps, mushroom-and-loop fasteners, and the like. A cooperating side panel member can be associated with each fastener and may be constructed to be nonelasticized, or to be elastically stretchable at least along the lateral direction of the diaper 20.

To provide improved fit and to help reduce leakage of body exudates from the diaper 20, at least the side margins 38 of the diaper are elasticized. For example, the side margins 38 may be constructed to operably gather and shirr the side edges 28 of the diaper 20 to provide elasticized leg bands which can closely fit around the legs of the wearer to reduce leakage and provide improved comfort and appearance. Similarly, the waist margins 40 can be employed to gather and shirr the end edges 30 of the diaper 20 to provide elasticized waistbands. The elasticized waistbands may be configured to operably gather and shirr the waist edges 30 of the diaper 20 to provide a resilient, comfortably close fit around the waist of the wearer. In FIG. 2, the leg and waist margins 38 and 40 are illustrated in their uncontracted, stretched condition for the purpose of clarity.

The diaper 20 may also include a pair of elasticized, longitudinally extending containment flaps (not shown) which are configured to maintain an upright, perpendicular arrangement in at least the intermediate section 26 of the diaper 20 to serve as an additional barrier to the lateral flow of body exudates. The diaper 20 may further include a surge management layer (not shown) positioned between the bodyside liner 34 and the absorbent body 36 which is configured to efficiently hold and distribute liquid exudates to the absorbent body 36. The surge management layer can prevent the liquid exudates from pooling and collecting on the portion of the diaper positioned against the wearer's skin, thereby reducing the level of skin hydration. Suitable constructions and arrangements of containment flaps and surge management layers are well known to those skilled in the art. Other suitable diaper components may also be incorporated on absorbent articles of the present invention.

The diaper 20 may be of various suitable shapes. For example, the diaper may have an overall rectangular shape, T-shape or an approximately hour-glass shape. In the shown embodiment, the diaper 20 has a generally I-shape. Examples of diaper configurations suitable for use in connection with the instant application and other diaper components suitable for use on diapers are described in U.S. Pat. No. 4,798,603 issued Jan. 17, 1989, to Meyer et al.; U.S. Pat. No. 5,176,668 issued Jan. 5, 1993, to Bernardin; U.S. Pat. No. 5,176,672 issued Jan. 5, 1993, to Bruemmer et al.; U.S. Pat. No. 5,192,606 issued Mar. 9, 1993, to Proxmire at al., and U.S. Pat. No. 5,509,915 issued Apr. 23, 1996, to Hanson et al., the disclosures of which are herein incorporated by reference. The various aspects and configurations of the invention can provide distinctive combinations of softness, body conformity, reduced red-marking of the wearer's skin, reduced skin hydration, and improved containment of body exudates.

The various components of the diaper 20 are integrally assembled together employing various types of suitable attachment means, such as adhesive, sonic bonds, thermal bonds or combinations thereof. In the shown embodiment, for example, the bodyside liner 34 and outer cover 32 are assembled to each other and to the absorbent body 38 with adhesive, such as a hot melt, pressure-sensitive adhesive. The adhesive may be applied as a uniform continuous layer of adhesive, a patterned layer of adhesive, a sprayed pattern of adhesive, or an array of separate lines, swirls or dots of adhesive. Similarly, other diaper components, such as the fasteners 42, may be assembled into the diaper 20 article by employing the above-identified attachment mechanisms.

The outer cover 32 of the diaper 20, as representatively illustrated in FIG. 2, may suitably be composed of a material which is either liquid permeable or liquid impermeable. It is generally preferred that the outer cover 32 be formed from a material which is substantially impermeable to liquids. The bodyside liner 34 suitably presents a bodyfacing surface which is compliant, soft feeling, and nonirritating to the wearer's skin. Further, the bodyside liner 34 may be less hydrophilic than the absorbent body 38, to present a relatively dry surface to the wearer, and may be sufficiently porous to be liquid permeable, permitting liquid to readily penetrate through its thickness.

In the different aspects of the present invention, the composite material 10 described above can provide the outer cover 32 and/or bodyside liner 34 or other components of the diaper 20 which are desired to have elastic properties such as the containment flaps or portions thereof. For example, the composite material 10, as representatively illustrated in FIG. 1, may provide the outer cover 32 of the diaper 20 illustrated in FIG. 2. In such a configuration, the elasticized portions 16 of the composite material may provide the elasticized side margins 38 or end margins 40 of the diaper 20. As discussed above, the use of such microwave activation can lead to improved processability. In particular, activating the selected portions of the composite material 10 after the diaper 20 has been assembled together eliminates the tension and retraction forces which would otherwise act on the web of interconnected diapers if conventional prestretched elastic segments were applied to the web.

The outer cover 32 is desirably provided by the composite material 10 as illustrated in FIG. 1 and described above. Alternatively, if the outer cover 32 does not need to be elastically contractible, the outer cover 32 can be manufactured from a thin plastic film or other flexible liquid-impermeable material which may or may not be temperature sensitive. For example, the outer cover 32 may be formed from a polyethylene film having a thickness of from about 0.012 millimeter (0.5 mil) to about 0.051 millimeter (2.0 mils). If it is desired to present the outer cover with a more clothlike feeling, the outer cover 32 may comprise a polyolefin film having a nonwoven web laminated to the outer surface thereof, such as a spunbond web of poylolefin fibers. For example, a stretch-thinned polypropylene film having a thickness of about 0.015 millimeter (0.6 mil) may have thermally laminated thereto a spunbond web of polypropylene fibers, which fibers have a thickness of about 1.5 to 2.5 denier per filament, which nonwoven web has a basis weight of about 17 grams per square meter (0.5 ounce per square yard). Methods of forming such clothlike outer covers are known to those skilled in the art.

Further, the outer cover 32 may be formed of a woven or nonwoven fibrous web layer which has been totally or partially constructed or treated to impart a desired level of liquid impermeability to selected regions that are adjacent or proximate the absorbent body 36. Still further, the outer cover 32 may optionally be composed of a micro-porous "breathable" material which permits vapors to escape from the absorbent body 36 while still preventing liquid exudates from passing through the outer cover 32. The outer cover 32 can also be embossed or otherwise provided with a matte finish to provide a more aesthetically pleasing appearance. The outer cover 32 may also be a temperature sensitive material such as, for example, a biaxial polyethylene which may shrink or retract when subjected to heat or microwave energy.

The bodyside liner 34 may be provided by the composite material 10 as illustrated in FIG. 1 and described above. Alternatively, if the bodyside liner 34 does not need to include elasticized portions, the bodyside liner 34 may be manufactured from a wide selection of other web materials, such as porous foams, reticulated foams, apertured plastic films, natural fibers (for example, wood or cotton fibers), synthetic fibers (for example, polyester or polypropylene fibers), or a combination of natural and synthetic fibers. The bodyside liner 34 is suitably employed to help isolate the wearers skin from liquids held in the absorbent body 36.

Various woven and nonwoven fabrics can be used for the bodyside liner 34. For example, the bodyside liner may be composed of a meltblown or spunbonded web of polyolefin fibers. The bodyside liner may also be a bonded-carded web composed of natural and/or synthetic fibers. The bodyside liner may be composed of a substantially hydrophobic material, and the hydrophobic material may, optionally, be treated with a surfactant or otherwise processed to impart a desired level of wettability and hydrophilicity. In a particular embodiment of the present invention, the bodyside liner 34 comprises a nonwoven, spunbond, polypropylene fabric composed of about 2.8–3.2 denier fibers formed into a web having a basis weight of about 20 grams per square meter and a density of about 0.13 gram per cubic centimeter. The fabric may be surface treated with about 0.28 weight percent of a surfactant commercially available from the Rohm and Haas Co. under the trade designation Triton X-102. The surfactant may be applied by any conventional means, such as spraying, printing, brush coating or the like. The surfactant may be applied to the entire bodyside liner 34 or may be selectively applied to particular sections of the bodyside liner 34, such as the medial section along the longitudinal centerline of the diaper, to provide greater wettability of such sections.

The absorbent body 36 of the diaper 20, as representatively illustrated in FIG. 2, may suitably comprise a matrix of hydrophilic fibers, such as a web of cellulosic fluff, mixed with particles of a high-absorbency material commonly known as superabsorbent material. In a particular embodiment, the absorbent body 36 comprises a matrix of cellulosic fluff, such as wood pulp fluff, and superabsorbent hydrogel-forming particles. The wood pulp fluff may be exchanged with synthetic, polymeric, meltblown fibers or with a combination of meltblown fibers and natural fibers. The superabsorbent particles may be substantially homogeneously mixed with the hydrophilic fibers or may be non-uniformly mixed. The fluff and superabsorbent particles may also be selectively placed into desired zones of the absorbent body 36 to better contain and absorb body exudates. The concentration of the superabsorbent particles may also vary through the thickness of the absorbent body 36. Alternatively, the absorbent body 36 may comprise a laminate of fibrous webs and superabsorbent material or other suitable means of maintaining a superabsorbent material in a localized area.

The absorbent body 36 may have any of a number of shapes. For example, the absorbent core may be rectangular, I-shaped, or T-shaped. It is generally preferred that the absorbent body 36 be narrower in the crotch area than in the front or rear portions of the diaper 20. The size and the absorbent capacity of the absorbent body 36 should be compatible with the size of the intended wearer and the liquid loading imparted by the intended use of the absorbent article.

The high-absorbency material can be selected from natural, synthetic, and modified natural polymers and materials. The high-absorbency materials can be inorganic materials, such as silica gels, or organic compounds, such as crosslinked polymers. The term "crosslinked" refers to any means for effectively rendering normally water-soluble materials substantially water insoluble but swellable. Such means can include, for example, physical entanglement, crystalline domains, covalent bonds, ionic complexes and associations, hydrophilic associations such as hydrogen bonding, and hydrophobic associations or Van der Waals forces.

Examples of synthetic, polymeric, high-absorbency materials include the alkali metal and ammonium salts of poly (acrylic acid) and poly(methacrylic acid), poly (acrylamides), poly(vinyl ethers), maleic anhydride copolymers with vinyl ethers and alpha-olefins, poly(vinyl pyrolidone), poly(vinyl morpholinone), poly(vinyl alcohol), and mixtures and copolymers thereof. Further polymers suitable for use in the absorbent core include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthum gum, locust bean gum, and the like. Mixtures of natural and wholly or partially synthetic absorbent polymers can also be useful in the present invention. Such high-absorbency materials are well known to those skilled in the art and are widely commercially available. Examples of superabsorbent polymers suitable for use in the present invention are SANWET IM 3900 polymer available from Hoechst Celanese located in Portsmouth, Va. and DOW DRYTECH 2035LD polymer available from Dow Chemical Co. located in Midland, Mich.

The high absorbency material may be in any of a wide variety of geometric forms. As a general rule, it is preferred that the high absorbency material be in the form of discrete particles. However, the high absorbency material may also be in the form of fibers, flakes, rods, spheres, needles, or the like. As a general rule, the high absorbency material is present in the absorbent body in an amount of from about 5 to about 90 weight percent based on total weight of the absorbent body 36.

Optionally, a substantially hydrophilic tissue wrapsheet (not illustrated) may be employed to help maintain the integrity of the airlaid fibrous structure of the absorbent body 36. The tissue wrapsheet is typically placed about the absorbent body over at least the two major facing surfaces thereof and composed of an absorbent cellulosic material, such as creped wadding or a high wet-strength tissue. In one aspect of the invention, the tissue wrapsheet can be configured to provide a wicking layer which helps to rapidly distribute liquid over the mass of absorbent fibers comprising the absorbent body. In another aspect of the invention, the wrapsheet material on one side of the absorbent fibrous mass may be bonded to the wrapsheet located on the opposite side of the fibrous mass.

Figure 3:
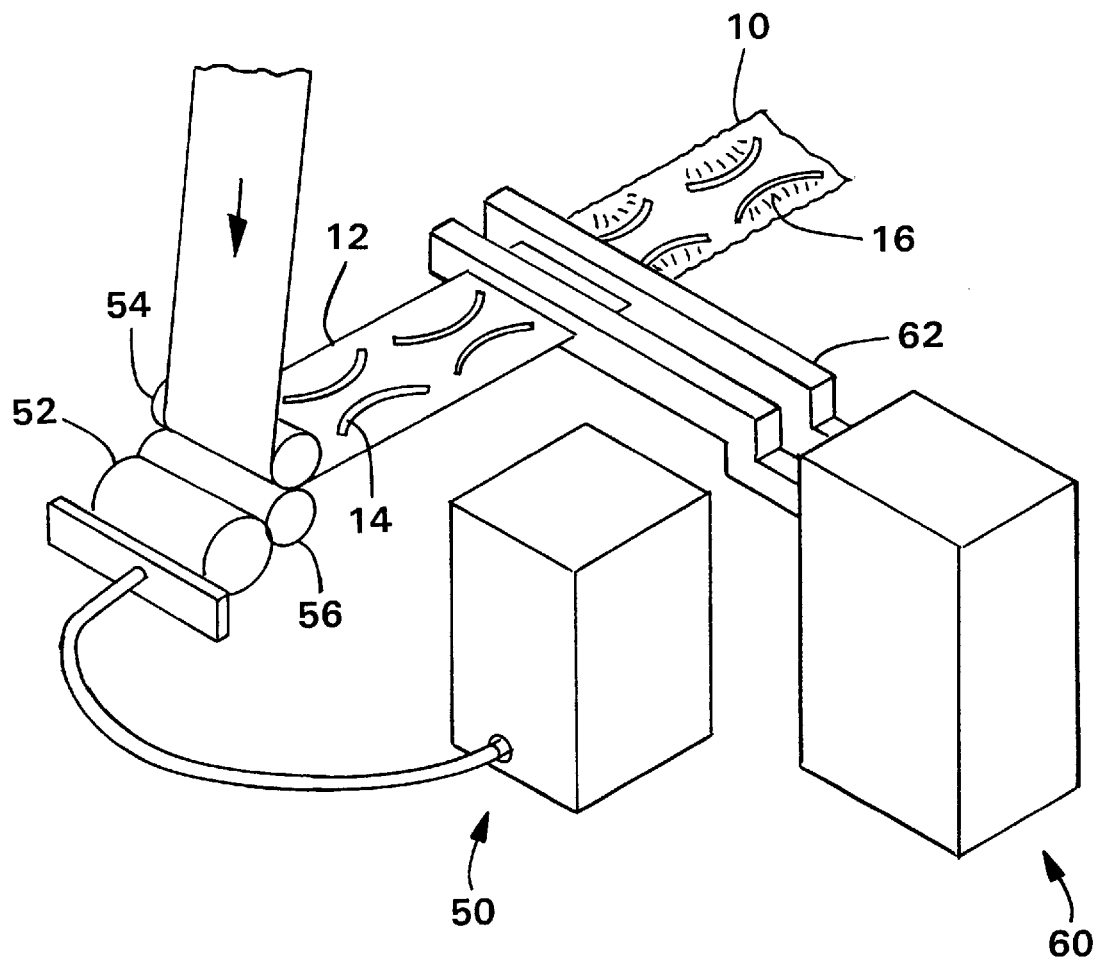
FIG. 3 representatively shows a perspective view of a method according to one embodiment of the invention.

With reference to FIG. 3, a method of making a composite material having elasticized portions according to one embodiment of the invention is representatively illustrated. The composite material 10 is provided by applying a microwave sensitive material 14 to at least one temperature sensitive elastic material 12 and subjecting the composite material to microwave energy. For example, as illustrated in FIG. 3, a web of the temperature sensitive elastic material 12 is supplied at a substantially continuous rate. For improved manufacturing efficiency, the web of elastic material 12 is desirably supplied at a speed of at least about 200 meters per minute and more desirably at a speed of at least about 300 meters per minute.

The microwave sensitive material 14 is applied to the web of elastic material 12 as it is continuously moving. In the illustrated embodiment, the microwave sensitive material 14 is a liquid which is applied to the elastic material 12 using conventional printing equipment well known to those skilled in the art. For example, an application module 50 may supply and apply the liquid microwave sensitive material 14 to an applicator roll 52. The applicator roll 52 in turn transfers the material 14 to one of a pair of nip rolls 54 and 56 through which the web of temperature sensitive elastic material 12 passes. Thus, the microwave sensitive material 14 is transferred to selected regions of the elastic material 12. Alternatively, the liquid microwave sensitive material 14 may be sprayed or coated onto the elastic material 12 using conventional technology well known to those skilled in the art.

The microwave sensitive material 14 may be applied continuously along the entire length of the elastic material 12 or intermittently to provide the selected regions which will retract and become elasticized upon the application of microwave energy. For example, if the web of temperature sensitive elastic material 12 is to be used in an absorbent article, such as for the outer cover of the diaper illustrated in FIG. 2, the microwave sensitive material 14 may be applied intermittently along the side edges of the web of elastic material 12 to provide the selected region. In such a configuration, the intermittent, selected regions to which the microwave sensitive material 14 have been applied can provide elasticized leg portions of the article. Alternatively, the microwave sensitive material 14 may be applied laterally across at least a portion of the web of elastic material 12 at intermittent locations along the length of the web 12 to provide elasticized waist portions of the article. The microwave sensitive material 14 may otherwise be applied to the elastic material 12 to provide other elasticized components of the diaper such as containment flaps.

The various methods of applying the microwave sensitive material 14 to the elastic material 12 discussed above should not subject the elastic material 12 to high temperatures. Desirably, the microwave sensitive material 14 is applied at a temperature which is less than the relaxation temperature of the temperature sensitive elastic material 12 such that the elastic material 12 is not activated during the application process.

The composite web 10 including the temperature sensitive elastic material 12 with the microwave sensitive material 14 thereon is then subjected to microwave energy. For example, as representatively illustrated in FIG. 3, a microwave generator 60 may supply microwave energy to at least one microwave cavity 62 through which the composite material 10 is continuously passed. A suitable microwave generator and cavity is described in U.S. Pat. No. 5,536,921 issued Jul. 16, 1996, to Hedrick et al. which is hereby incorporated by reference. Such a generator typically provides a plurality of microwave standing waves within an enclosure or cavity, such as the microwave cavity 62 illustrated in FIG. 3. The web of material can then be passed through the standing waves where the incident microwave energy can be converted into heat within the web.

Microwave energy is supplied, continuously or intermittently, to the continuously moving web of temperature sensitive elastic material 12 at a rate which activates the selected regions 16 on the web 12. The rate at which the energy is supplied is dependent upon the types of elastic material 12 and microwave sensitive material 14 and the speed at which the composite material 10 is moving. In general, to provide sufficient energy to the web traveling at speeds of greater than 200 meters per second, it is desirable that the generator 60 supply microwave energy of about 2450 Mhz at least about 300 and more desirably at least about 500 watts to the web 12 for about 0.08 to about 0.8 seconds. The generator 60 may also be configured to provide a variable amount of microwave energy relative to the speed of the web such that the energy provided increases as the web speed increases. To provide such high levels of energy in such a short time period, it may be desirable to have more than one microwave cavity through which the web 12 passes. For example, the system may include from 2 to 20 cavities through which the web 12 passes to provide the necessary energy to activate the selected regions 16 on the web of elastic material 12.

The combination of the speed of the web of temperature sensitive elastic material 12 and the temperature at which the elastic material retracts defines the heating rate at which the selected regions on the elastic material must be heated to achieve retraction. In a process for producing a web of interconnected absorbent articles such as diapers it is desired that the microwave system be capable of providing a heating rate of at least about 50 degrees Centigrade per second and more desirably from about 50 to about 500 degrees Centigrade per second to accommodate the desired manufacturing speed.

Compared to conventional systems which have used heated air or heated rolls to activate webs or individual pieces of latent elastic material, the use of microwave energy is less expensive, easier to control, and faster to provide improved manufacturing efficiency and quality. For example, in a manufacturing process for absorbent articles such as diapers, the entire diaper article may be manufactured while the elastic material 12 is in a latent state for improved control of the web of interconnected articles through the machine. After all or a majority of the components have been assembled on the articles, the microwave energy can be supplied to the web thereby activating the selected regions 16 on the elastic material 12. In such a configuration, the microwave energy may be applied to the web of interconnected articles just prior to severing the web into individual articles such that the web is severed before the retraction of the selected regions 16 of the elastic material 12 has occurred. In this manner it is not required to apply great amounts of tension to the web of interconnected articles as it passes through the machine as is required in conventional systems which utilize elastic segments which are applied to the web in a prestretched condition. In such conventional systems, the elastic segments have acted to constrict and gather the web of interconnected articles making the web difficult to control and complicating the process of adding any additional features to the web.

Moreover, the use of such microwave activation of selected regions eliminates the need for complex equipment which has been required in conventional systems to insert longitudinal or transverse pieces of elastic material. Such equipment has been particularly complex if it is desired to place the pieces of elastic material in a prestretched or elongated state in the proper locations on the web.

The following Examples are presented to provide a more detailed understanding of the invention. The Examples are intended to be representative, and are not intended to limit the scope of the invention.

EXAMPLE

A elastomeric material commercially available from Elf Atochem, a business having offices located in Philadelphia, Pa., under the trade designation PEBAX 2533 was stretched 490% and annealed. The stretched, annealed material was laminated between two webs of spunbond polypropylene fibers, each having a basis weight of about 2 grams per square meter using an adhesive commercially available from Findley Adhesive, a business having offices located in Milwaukee, Wis., under the trade designation H2525A to provide the latent elastic composite.

Approximately 1 cubic centimeter of microwave responsive solution was applied to the composite in a selected region. The solution was absorbed directly into the composite. The solution included the following ingredients by weight:

| | | |
|---|---|---|
| polyethylene glycol | 32.7% | |
| sorbitol | 32.6% | |
| sodium chloride | 1.7% | |
| water | 33.1% | |
| surfactant (Triton X-100) | trace | |

The treated composite was placed in a conventional microwave cooking oven commercially available from Sharp, Incorporated under the trade designation Sharp Carousel for about 5 seconds on the high setting. The selected region of the composite to which the microwave responsive solution was applied retracted approximately 50–100% and produced a well defined gathering.

Having thus described the invention in rather full detail, it will be readily apparent to a person of ordinary skill that various changes and modifications can be made without departing from the spirit of the invention. All of such changes and modifications are contemplated as being within the scope of the present invention as defined by the subjoined claims.

We claim:

1. A composite material having elasticized portions comprising:
   a) a temperature sensitive elastic material; and
   b) a microwave sensitive material located on selected regions of said temperature sensitive elastic material to provide said composite material wherein said elasticized portions in said composite material are provided by applying microwave energy to said composite material thereby activating said temperature sensitive elastic material adjacent said microwave sensitive material.

2. The composite material according to claim 1 wherein said temperature sensitive elastic material is a film material.

3. The composite material according to claim 1 wherein said microwave sensitive material is a solution.

4. The composite material according to claim 1 wherein said microwave sensitive material defines a relative dielectric loss factor which is greater than a relative dielectric loss factor of said temperature sensitive elastic material.

5. The composite material according to claim 1 wherein said microwave sensitive material defines a relative dielectric loss factor which is less than a relative dielectric loss factor of said temperature sensitive elastic material.

6. The composite material according to claim 1 wherein a ratio of a relative dielectric loss factor of said microwave sensitive material to a relative dielectric loss factor of said temperature sensitive elastic material is at least about 5.

7. The composite material according to claim 1 wherein said elasticized portions of said composite material define an elongation of at least about 25 percent.

8. The composite material according to claim 7 wherein portions of said composite material opposite said elasticized portions define an elongation of no more than about 20 percent.

9. A garment article comprising the composite material of claim 1.

10. An absorbent article having elasticized portions, said article comprising:
    a) at least one temperature sensitive elastic material;
    b) an absorbent layer located in superposed relation to said temperature sensitive elastic material; and
    c) a microwave sensitive material located on selected regions of said temperature sensitive elastic material wherein said selected regions of said temperature sensitive elastic material have been activated by applying microwave energy to said temperature sensitive elastic material thereby heating said microwave sensitive material to create said elasticized portions.

11. The absorbent article of claim 10 wherein said temperature sensitive elastic material includes a poly(ethylene-oxide)-co-poly(amide) copolymer and a poly(ethylene-hexene) copolymer.

12. The absorbent article of claim 10 wherein said microwave sensitive material is selected from the group consisting of a polyacrylate solution, a polyamide solution, a polyvinyl methyl ether solution, a polyamide hot melt adhesive, and a polyvinyl methyl based hot melt adhesive.

13. The absorbent article of claim 10 wherein said microwave sensitive material defines a relative dielectric loss factor which is greater than a relative dielectric loss factor of said temperature sensitive elastic material.

14. The absorbent article of claim 10 wherein a ratio of a relative dielectric loss factor of said microwave sensitive material to a relative dielectric loss factor of said temperature sensitive elastic material is at least about 5.

15. The absorbent article of claim 10 wherein said elasticized portions of said absorbent article define an elongation of at least about 25 percent.

16. The absorbent article of claim 10 wherein said elasticized portions of said absorbent article are located adjacent leg openings in said absorbent article.

17. The absorbent article of claim 10 wherein said elasticized portions of said absorbent article are located adjacent a waist opening in said absorbent article.

18. The absorbent article of claim 10 wherein said temperature sensitive elastic material provides an outer cover layer for said absorbent article which is intended to be positioned opposite a wearer's body in use.

19. The absorbent article of claim 10 wherein said temperature sensitive elastic material provides a bodyside liner layer for 'said absorbent article which is intended to contact a wearer's body in use.

20. A method of making a composite material having elasticized portions comprising:
   a) supplying a web of temperature sensitive elastic material;
   b) applying a microwave sensitive material to selected regions of said web of temperature sensitive elastic material to provide said composite material; and
   c) applying microwave energy to said composite material thereby activating said temperature sensitive elastic material adjacent said microwave sensitive material to create said elasticized portions in said composite material.

21. The method according to claim 20 wherein said web of temperature sensitive elastic material is continuously supplied at a speed of at least about 200 meters per minute.

22. The method according to claim 20 wherein said microwave sensitive material is applied to an entire length of said web of temperature sensitive material to provide continuous elasticized portions.

23. The method according to claim 20 wherein said microwave sensitive material is intermittently applied to said selected regions of said web of temperature sensitive elastic material to provide intermittent elasticized portions in said composite material.

24. The method according to claim 20 wherein said microwave energy is applied to said composite material at a rate of at least about 300 watts.

25. The method according to claim 20 wherein said microwave sensitive material defines a relative dielectric loss factor which is greater than a relative dielectric loss factor of said web of temperature sensitive elastic material.

26. The method according to claim 20 wherein said microwave sensitive material defines a relative dielectric loss factor which is less than a relative dielectric loss factor of said web of temperature sensitive elastic material.

27. The method according to claim 20 wherein a ratio of a relative dielectric loss factor of said microwave sensitive material to a relative dielectric loss factor of said web of temperature sensitive elastic material is at least about 5.

28. The method according to claim 20 wherein said elasticized portions of said composite material define an elongation of at least about 25 percent.

29. The method according to claim 28 wherein portions of said composite material opposite said elasticized portions define an elongation of no more than about 20 percent.

30. The method according to claim 20 wherein said web of temperature sensitive elastic material includes a poly (ethylene-oxide)-co-poly(amide) copolymer and a poly (ethylenehexene) copolymer.

31. The method according to claim 20 wherein said microwave sensitive material is selected from the group consisting of a polyacrylate solution, a polyamide solution, a polyvinyl methyl ether solution, a polyamide hot melt adhesive, and a polyvinyl methyl based hot melt adhesive.

32. A method of making an absorbent article having elasticized portions comprising the steps of:
   a) continuously supplying at least one web of temperature sensitive elastic material;
   b) securing an absorbent layer in superposed relation to said web of temperature sensitive elastic material;
   c) applying a microwave sensitive material to selected regions of said web of temperature sensitive elastic material;
   d) heating said microwave sensitive material by applying microwave energy to said web of temperature sensitive elastic material thereby activating said selected regions of said web of temperature sensitive elastic material to create said elasticized portions; and
   e) intermittently severing said continuous web of temperature sensitive elastic material to provide said absorbent article.

33. The method according to claim 32 wherein said web of temperature sensitive elastic material is continuously supplied at a speed of at least about 200 meters per minute.

34. The method according to claim 32 wherein said microwave sensitive material is intermittently applied to said selected regions of said web of temperature sensitive elastic material to provide intermittent elasticized portions.

35. The method according to claim 32 wherein said microwave sensitive material is intermittently applied along opposite side edges of said web of temperature sensitive elastic material to provide elasticized leg portions of said absorbent article.

36. The method according to claim 32 wherein said microwave sensitive material is applied laterally across at least a portion of said web of temperature sensitive elastic material at intermittent locations along a length of said web of temperature sensitive elastic material to provide elasticized waist portions of said absorbent article.

37. The method according to claim 32 wherein said microwave sensitive material defines a relative dielectric loss factor which is greater than a relative dielectric loss factor of said web of temperature sensitive elastic material.

38. The method according to claim 37 wherein a ratio of said relative dielectric loss factor of said microwave sensitive material to said relative dielectric loss factor of said web of temperature sensitive elastic material is at least about 5.

39. The method according to claim 32 wherein said elasticized portions of said absorbent article define an elongation of at least about 25 percent.

* * * * *